(12) United States Patent
Nishimura et al.

(10) Patent No.: US 6,994,833 B1
(45) Date of Patent: Feb. 7, 2006

(54) REACTOR FOR CATALYTIC GAS PHASE OXIDATION

(75) Inventors: Takeshi Nishimura, Himeji (JP); Masakatsu Mori, Hyogo (JP); Masatsugu Kitaura, Himeji (JP); Osamu Dodo, Hyogo (JP); Michio Tanimoto, Himeji (JP)

(73) Assignee: Nippon Shokubai Co., LTD., Osaka (JP)

( * ) Notice: Subject to any disclaimer, the term of this patent is extended or adjusted under 35 U.S.C. 154(b) by 599 days.

(21) Appl. No.: 09/705,679

(22) Filed: Nov. 3, 2000

(30) Foreign Application Priority Data

Nov. 5, 1999 (JP) .................................. 11-315469

(51) Int. Cl.
*B01J 8/04* (2006.01)

(52) U.S. Cl. ...................... 422/196; 422/197; 422/201; 422/202; 422/205; 422/211; 422/312; 422/81; 422/140; 422/161; 422/162

(58) Field of Classification Search ................ 422/196, 422/197, 201, 202, 205, 211, 312, 81, 140, 422/161, 162; 165/81, 140, 162
See application file for complete search history.

(56) References Cited

U.S. PATENT DOCUMENTS

| | | | |
|---|---|---|---|
| 2,986,454 A | 5/1961 | Jewett | |
| 3,147,084 A | 9/1964 | Franzen et al. | 23/288 |
| 4,142,581 A * | 3/1979 | Yoshitomi et al. | 165/173 |
| 4,203,906 A | 5/1980 | Takada et al. | 260/346.4 |
| 4,256,783 A * | 3/1981 | Takada et al. | 422/197 |
| 4,436,146 A * | 3/1984 | Smolarek | 165/111 |
| 5,048,601 A | 9/1991 | Yamaguchi et al. | 165/140 |
| 5,759,500 A | 6/1998 | Garner et al. | |

FOREIGN PATENT DOCUMENTS

| | | |
|---|---|---|
| EP | 198 06 810 A | 1/1980 |
| EP | 28 30 765 A | 3/1980 |
| EP | 0 911 313 A | 4/1999 |

* cited by examiner

Primary Examiner—Glenn Caldarola
Assistant Examiner—Alexis Wachtel
(74) Attorney, Agent, or Firm—Mathews, Sheperd, McKay & Bruneau, P.A.

(57) ABSTRACT

In a shell-and-tube type reactor, the leakage between the upper and lower chambers is substantially decreased by tightly fitting the reaction tubes to the shield. The present invention provides a reactor for use in catalytic gas phase oxidation characterized by expanding reaction tubes to at least one groove formed in the reaction tube-fixing part of an intermediate tube sheet to form a shield, thereby forming plural of chambers with the intermediate tube sheet, and forming an expansion joint around the periphery of each of the chambers.

9 Claims, 3 Drawing Sheets

REACTOR FOR CATALYTIC GAS PHASE OXIDATION

BACKGROUND OF THE INVENTION

1. Field of the Invention

This invention relates to a shell-and-tube heat exchanger type reactor having the interior of the shell thereof partitioned into a plurality of chambers, and to a method for the production of (meth)acrylic acid by the use of the reactor. More particularly, it relates to a shell-and-tube heat exchanger type reactor adapted to repress migration of a heat medium (heat transfer medium) between adjacent chambers partitioned with a shield, and to a method for the production of (meth)acrylic acid by the use of the reactor.

2. Description of the Related Art

Generally, a method for producing acrylic acid by the reaction of catalytic gas phase oxidation of propylene entails generation of a large amount of heat. For the purpose of controlling the reaction temperature within a fixed range or preventing the occurrence of hot spots (local spots of abnormally high temperature in the catalyst layer) within a reaction zone, a method for quickly absorbing or circulating such heat, for example, has been proposed.

JP-A-54-21966 discloses a shell-and-tube heat exchanger type reactor which is partitioned into two or more chambers by the use of shields and adapted to control the temperature of a heat medium by the use of a heat medium circulating system provided in each of the chambers. This reactor, though partitioned with the shields into vertically separate chambers, enables the heat media placed respectively in the vertically separate chambers to migrate into the adjacent chambers through the shield. Thus, it is not intended to shield the separate chambers substantially completely. Further, it is mentioned that when the reaction tubes and the shields happen to be fixed in close approximation, any temperature difference between the regions A and B or frequent use of the reactor for heating and cooling will bring disadvantages such as inducing the reaction tubes and the shields to develop thermal strain and suffering them to come into mutual contact and wear away.

JP-B-07-73674 discloses improvements in and concerning a vessel which is furnished with a partition plate to produce a plurality of chambers operating at different degrees of temperature, wherein the reaction of a high temperature and the quenching for rapidly cooling the product are respectively performed in the chambers.

SUMMARY OF THE INVENTION

An object of this invention is, therefore, to solve the problems of the prior art mentioned above and provide, in the shell-and-tube heat exchanger type reactor in which the interior of the reactor is partitioned with a shield into a plurality of chambers, a reactor for catalytic gas phase oxidation which substantially represses migration of the heat media between those chambers partitioned with shields and a method for the production of (meth)acrylic acid by the use of the reactor.

The object of this invention is achieved by, in a shell-and-tube heat exchanger type reactor the interior of which is partitioned with a shield into a plurality of chambers, a reactor for catalytic gas phase oxidation characterized by fitting reaction tubes in an expanded state to at least one groove disposed in reaction tube-fixing parts of the shield to form an intermediate tube sheet, thereby providing a plurality of chambers partitioned with the intermediate tube sheet, and further disposing expansion joints around the shells of the chambers.

The object of this invention is further achieved by a method for producing (meth)acrylic acid by using the reactor.

According to the reactor of this invention, since the intermediate tube sheet substantially seals the upper and the lower chambers and since the chambers are each provided around the shell thereof with the expansion joint, the temperature of the heat medium in each of the chambers can be readily maintained and controlled, the distortion of the reactor by heat can be reduced, and the heat generated by the reaction can be readily absorbed.

Further, according to the method of this invention, desired products can be produced in a high yield.

The above and other objects, features and advantages of the present invention will become clear from the following description of the preferred embodiments.

DETAILED DESCRIPTION OF THE PREFERRED EMBODIMENTS

Figure 1:
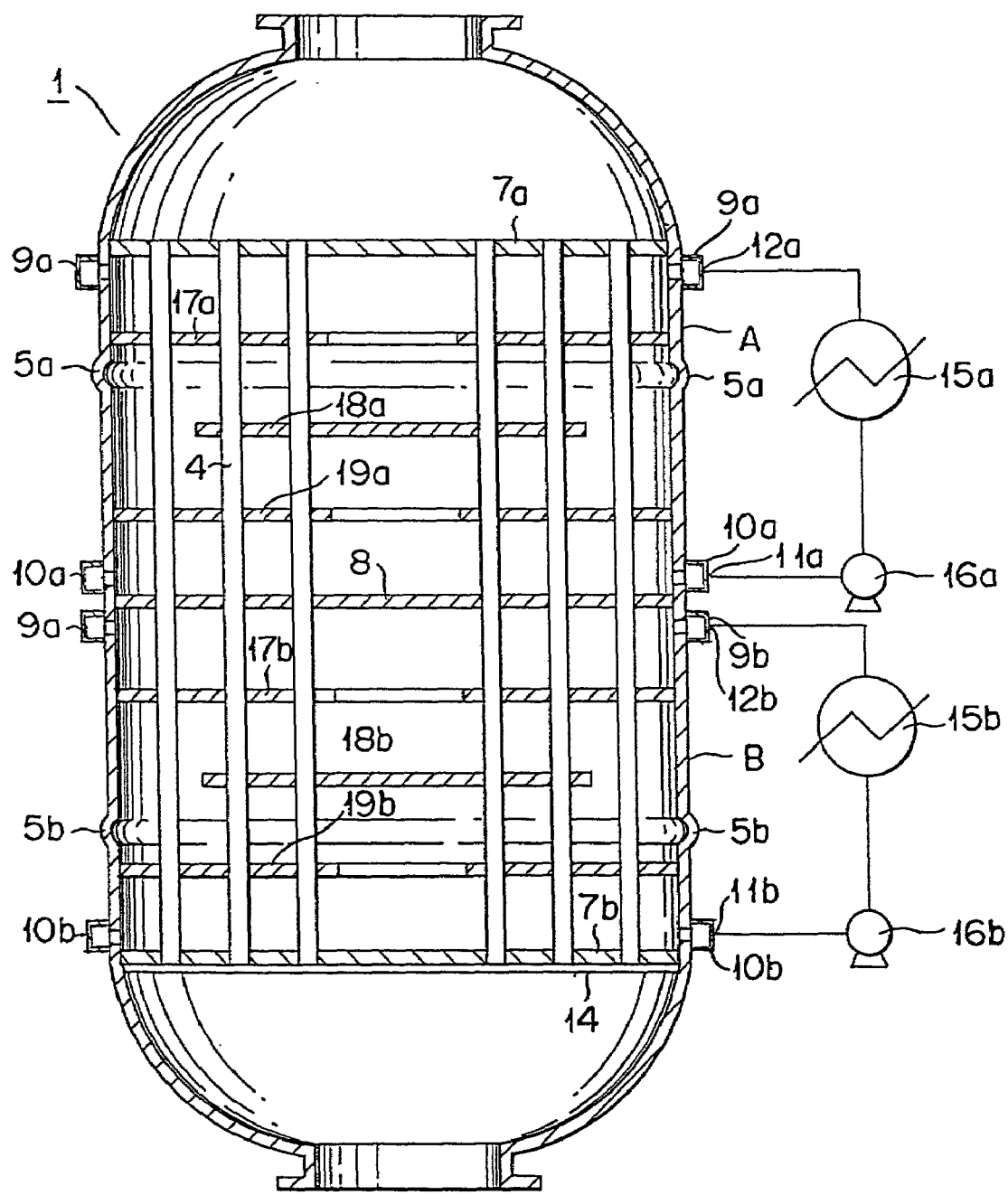
FIG. 1 is an explanatory diagram illustrating one example of the longitudinal cross section of the reactor of this invention for catalytic gas phase oxidation.

The shell-and-tube heat exchanger type reactor to be used in this invention is not particularly restricted so long as it is a shell-and-tube heat exchanger type reactor having the interior of the shell of the reactor (the outer side of the bundle of reaction tubes) partitioned with shields into a plurality of chambers. The conventional shell-and-tube heat exchanger type reactors having a circular or a polygonal cross section and adapted to absorb the heat generated by an exothermic reaction or supply the heat required for the reaction can be used. The shell-and-tube heat exchanger type reactor is preferred to be in the vertical type for introducing the raw material gas from above or from below.

The reactor is preferably provided in the shell thereof with a baffle plate capable of changing the transfer direction of a heat medium such as a molten salt, which is introduced into the shell. The term "baffle plate" as used herein refers to means for transferring a heat medium mainly in the lateral direction, such as one member or a combination of two or more members selected from the groups consisting of the known baffle plates shaped like discs, donut type discs, segmental discs, and orifices. More preferably, the reactor is provided with an annular conduit containing a plurality of openings for introducing and discharging a heat medium from and into the periphery of the reactor to reduce the temperature distribution of heat medium in the horizontal plane nearby the inlets and outlets for the heat medium.

The shell-and-tube heat exchanger type reactor is partitioned into, for example, two chambers in a substantially closed state. This closed state is achieved by expanding reaction tubes, i.e., part of reaction tubes facing to a groove, to at least one groove disposed in reaction tube-fixing parts of the tube sheet to form a shield, this tube sheet is referred to as "intermediate tube sheet". The substantially closed state established between the upper and lower chambers is generally secured by expanding part of the reaction tubes, which face to the grooves, to tightly fit the relevant grooves in the tube sheet. For the purpose of decreasing the leakage between the chambers, the reaction tube-fixing parts are preferably each provided with two grooves. When the reaction tube-fixing parts have an ample room, the number of such grooves formed therein may be increased to three or, when necessary, even to four or more.

The intermediate tube sheet is a plate which partitions the interior of shell, between the upper and lower ends of reaction tubes, in a substantially closed state into vertically separate spaces in the reactor. The installation of one intermediate tube sheet inside the reactor, wherefore, results in two vertically separate chambers. Though one intermediate tube sheet is generally installed, a plurality of such intermediate tube sheets may be optionally installed, depending on reaction conditions.

The reactor is provided almost horizontally around the shell or periphery of each of the chambers with a circular, expansion joint roughly semicircular in cross section, with the inner face of the joint directed toward the inner side of the reactor and the upper and lower ends of the joint connected to the almost horizontally cut shell of the reactor by a known method such as welding, and which joint is capable of absorbing the distortion generated by the increase or decrease of the heat of a heat medium. Since the expansion joint is capable of absorbing the distortion due to the heat, it can decrease the effect of heat on the whole reactor even when the each chamber has different degrees of temperature. The expansion joint, for the purpose of increasing the flexibility of the shell part of the reactor, may be made of a sheet of the same quality as the shell part of the reactor. The vertical position for mounting the expansion joint is preferred to fall between a tube sheet and a baffle plate or between adjacent baffle plates because the expansion joint is connected to the shell of the reactor by welding.

Since in this invention the chambers are each provided with an expansion joint and the reaction tubes are fitted in an expanded state to at least one groove provided in the reaction tube-fixing part of the tube sheet, the tightly fitted parts receive relatively slightly to a thermal effect, unlike a method which fixes tubes to the shield by welding, even when the operation of heating and cooling is frequently performed in the reactor. The temperature difference between the chambers is preferably not more than 100° C. (not including zero) from the viewpoint of avoiding thermal strain.

Further, the amount of water migrated from the upper chamber to the lower chamber which are partitioned with an intermediate tube sheet is preferred to satisfy the relation, amount of leakage (ml/hour per reaction tube)$\leq 1.27\times 10^{-5}$ pressure difference (Pa) {1.25×pressure difference (kg/cm$^2$)}, preferably amount of leakage (ml/hour per reaction tube) $\leq 1.02\times 10^{-5}$×pressure difference (Pa) {0.01×pressure difference (kg/cm$^2$)}, as determined by a test for hydraulic pressure. Here, the term "pressure difference" means the pressure difference above and below the intermediate tube sheet. The amount of leakage varies with the pressure difference above and below the intermediate tube sheet; the degree of closure between the two chambers decreases in accordance as the amount of leakage increases and it increases in accordance as the amount of leakage decreases. The amount of leakage just defined applies similarly hereinafter. If this relation is not satisfied, it will hardly ignore the leakage of the heat medium from the upper chamber to the lower chamber, be very difficult to control the temperatures of the upper and lower chambers respectively, consequently not control the reaction temperature sufficiently, thereby failing to produce the desired product at an expected yield.

The amount of water transferred from the lower chamber to the upper chamber which are partitioned with the intermediate tube sheet is preferred to satisfy the relation, amount of leakage (ml/hour per reaction tube)$\leq 1.27\times 10^{-5}$×pressure difference (Pa) {1.25×pressure difference (kg/cm$^2$)}, preferably amount of leakage (ml/hour per reaction tube) $\leq 1.02$×pressure difference (Pa) {0.01×pressure difference (kg/cm$^2$)}, as determined by a test for hydraulic pressure. If this relation is not satisfied, it will hardly ignore the leakage of the heat medium from the lower chamber to the upper chamber, be very difficult to control the temperatures of the upper and lower chambers respectively, consequently not control the reaction temperature sufficiently, thereby failing to produce the desired product at an expected yield.

Of course, it is more preferable that both the chambers satisfy the aforementioned conditions for the amounts of transfer of water.

Since the upper and lower chambers are partitioned in a substantially closed state with the intermediate tube sheet, the interiors of the upper and lower sections of the reaction tubes partitioned therewith allow a reaction to proceed at respectively different temperatures or allow respectively different reactions or treatments to proceed simultaneously. For example, the reaction that oxidizes propylene into acrolein on the upstream side and further oxidizes acrolein into acrylic acid on the downstream side may be cited. The position of the intermediate tube sheet may be properly decided. When the raw material gas is supplied through the upper part of the reactor, the upper part of the reactor constitutes itself the upstream side and the lower part the downstream side. Of course, the raw material gas may be supplied through the lower part of the reactor.

Now, this invention will be described more specifically below with reference to the accompanied drawings.

FIG. 1 is an explanatory diagram illustrating one example of the longitudinal cross section of the reactor of this invention, with two chambers, A and B. A reactor 1 has a circular cross section, and is installed in the interior thereof with a multiplicity of reaction tubes 4. These reaction tubes are fixed at their upper ends to an upper tube sheet 7a and at their lower ends to a lower tube sheet 7b respectively by a known method such as the technique of tube expansion or welding. The reactor 1 is provided around the shells of the chambers, A and B, respectively with expansion joints 5a, 5b. Further, the reactor 1 is preferably provided in the central part thereof devoid of a reaction tube 4 with a passage for forwarding a heat medium from the lower end upward so as to ensure efficient transfer of the heat medium. The shell side of the reactor 1 is partitioned into an upper and a lower section with an intermediate tube sheet 8 located at a nearly middle position between the upper and lower ends of the reaction tubes 4 to give two chambers, A and B.

Figure 2:
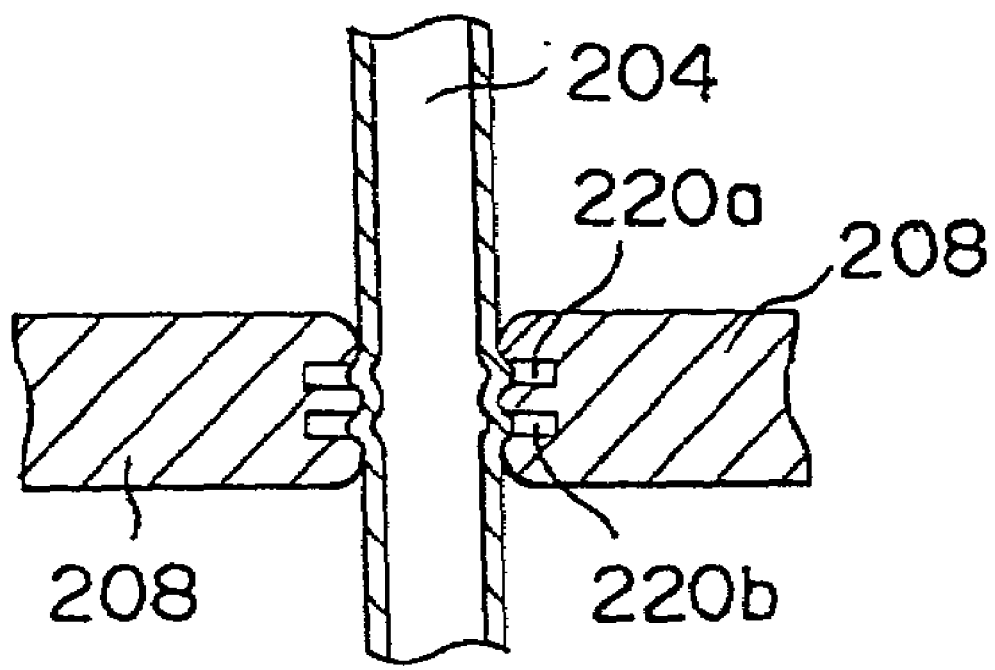
FIG. 2 is an explanatory diagram illustrating a magnified cross section of the fitting part of a reaction tube and an intermediate tube sheet.

FIG. 2 is a magnified, cross sectional, explanatory diagram illustrating the tightly fitted part between the reaction tube and the intermediate tube sheet. Referring to FIG. 2, an intermediate tube sheet 208 is provided with two grooves 220a, 220b and a reaction tube 204 tightly fitted to the grooves by the technique of tube expansion. The reaction tube 204 and the intermediate tube sheet 208 are preferably formed of the same material of steel or iron in consideration of possible expansion or shrink thereof by heating or cooling.

In the chambers, A and B, of FIG. 1, donut type baffle plates 17a, 17b, disc type baffle plates 18a, 18b, and donut type baffle plates 19a, 19b, for example, are alternately disposed for the purpose of dispersing the relevant heat media in the horizontal direction and reducing the temperature distribution in the horizontal direction.

The reaction tubes 4 may be packed with catalysts in a fixed bed for the purpose of reaction. For producing acrylic acid by the reaction of two-stage catalytic gas phase oxidation of a propylene-containing gas, for example, an oxidizing catalyst that is generally used for producing acrolein by the reaction of gas phase oxidation of a raw material gas containing propylene may be used as the catalyst on the upstream side. By the similar way, the catalyst on the downstream side is not particularly restricted. An oxidizing catalyst that is generally used for producing acrylic acid by the gas phase oxidation of a gas chiefly containing the acrolein obtained on the upstream side of the two-stage catalytic gas phase oxidation may be used.

Examples of the upstream side catalyst may include catalysts represented by the formula:

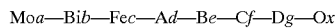

Mo$a$—Bi$b$—Fe$c$—A$d$—B$e$—C$f$—D$g$—O$x$ wherein
Mo, Bi, and Fe respectively denote molybdenum, bismuth, and iron,
A denotes at least one element selected from the group consisting of nickel and cobalt,
B at least one element selected from the group consisting of alkali metals and thallium,
C at least one element selected from the group consisting of phosphorus, niobium, manganese, cerium, tellurium, tungsten, antimony, and lead,
D at least one element selected from the group consisting of silicon, aluminum, zirconium, and titanium,
O oxygen, and
a, b, c, d, e, f, g, and x respectively denote the atomic ratios of Mo, Bi, Fe, A, B, C, D, and O which fall in the respective ranges of b=0.1–10, c=0.1–10, d=2–20, e=0.001–5, f=0–5, g=0–30, and x the value decided by the states of oxidation of the relevant elements when a=12 is fixed.

Then, examples of the downstream side catalyst may include catalysts represented by the formula:

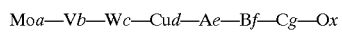

Mo$a$—V$b$—W$c$—Cu$d$—A$e$—B$f$—C$g$—O$x$ wherein
Mo denotes molybdenum, V vanadium, W tungsten, Cu copper,
A at least one element selected from the group consisting of antimony, bismuth, tin, niobium, cobalt, iron, nickel, and chromium,
B at least one element selected from the group consisting of alkali metal, alkaline earth metals, and thallium,
C at least one element selected from the group consisting of silicon, aluminum, zirconium, and cerium,
O oxygen, and
a, b, c, d, e, f, g, and x denote the atomic ratios respectively of Mo, V, W, Cu, A, B, C, and O which fall in the respectively ranges of b=2–14, c=0–12, d=0.1–5, e=0–5, f=0–5, g=0–10, and x the value decided by the states of oxidation of the relevant elements when a=12 is fixed.

Incidentally, the catalysts that form the upstream side catalyst bed and downstream side catalyst beds, do not need to be a simple catalyst each. For example, plural kinds of catalysts different in activity may be adopted and sequentially layered or, when necessary, such catalysts may be diluted with an inactive material such as an inactive carrier. This rule will similarly apply to the other catalysts, which will be described below.

The shape of the catalyst is not particularly restricted. The catalyst may be in the shape of Raschig rings, spheres, cylinders, and rings, for example. As the method for forming the catalyst of such a shape, carried molding, extrusion molding, and tablet molding may be adopted. Further, a catalyst that is obtained by depositing a catalytic substance on a refractory carrier is useful.

The reaction tubes 4 are equipped at the lower ends thereof with a wire mesh or a receptacle 14 for preventing the catalyst from falling before the catalyst is filled therein. The reaction tubes 4, when necessary, may be packed with a refractory material inactive in the relevant reaction before the catalyst is filled therein, and then an upstream side catalyst filled thereon. Subsequently, they are packed with a downstream side catalyst. A refractory material inactive in the relevant reaction may be interposed between the upstream side and downstream side catalysts.

Figure 3:
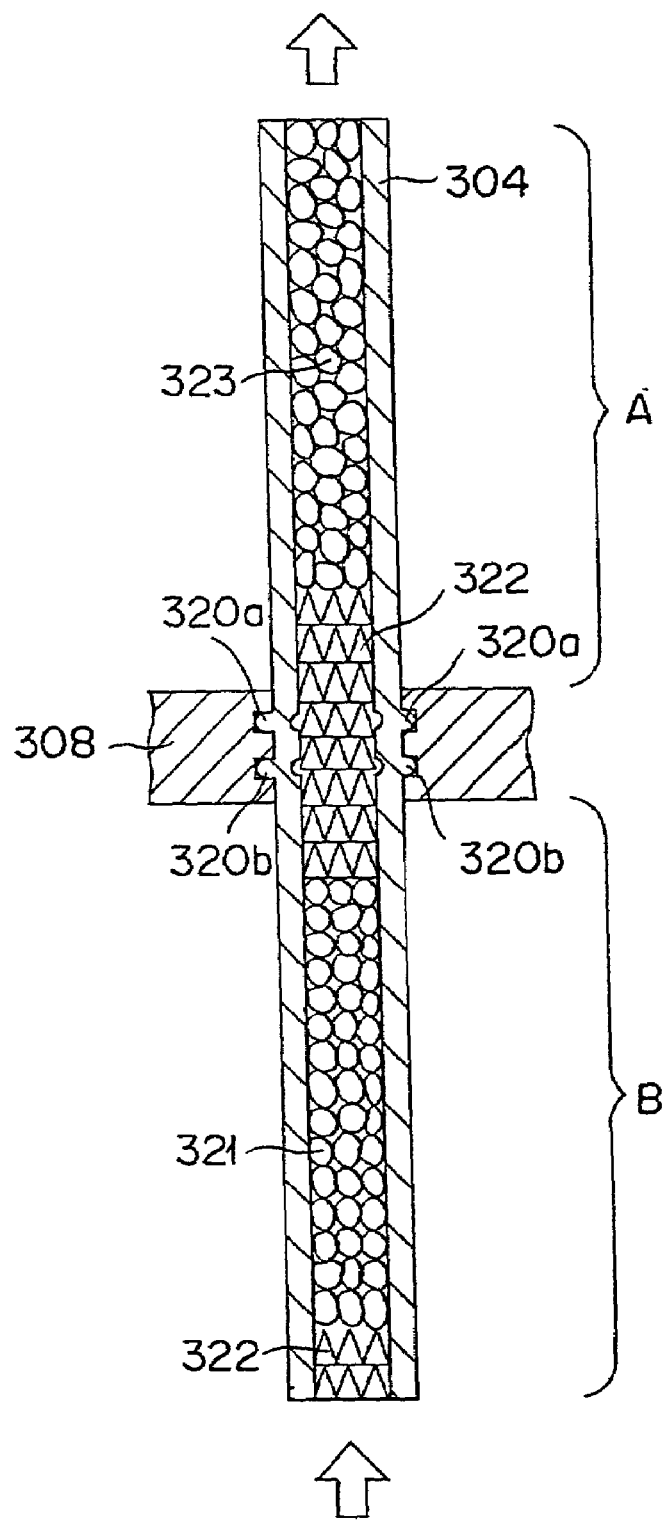
FIG. 3 is a schematic cross section illustrating one example of the packing of one reaction tube with a catalyst.

In FIG. 1, packing with the catalyst is omitted from easy perception of the drawing. FIG. 3 is a schematic cross section illustrating one example of the packing of one reaction tube with the catalyst. With reference to FIG. 3, the lower part of chamber B is packed with an inactive refractory substance 322 and an upstream side catalyst 321 sequentially, the upper part thereof extending via an intermediate tube sheet 308 up to part of chamber A is packed with an inactive refractory substance, and the remainder of chamber A is packed with a downstream side catalyst 323. When the temperature of chamber B is higher than that of chamber A, for example, the raw material gas is partially oxidized in the upstream side catalyst 321 layer, then cooled at the site of the inactive refractory substance 322 layer, and thereafter, further partially oxidized as retained at the temperature to which it is cooled at the site of the downstream side catalyst 323 layer to produce the desired product. That is, in chamber A, the site of the inactive refractory substance 322 corresponds to a cooling layer and the downstream side catalyst 323 corresponds to a reaction layer.

Examples of the inactive refractory substance may include α-alumina, alundum, mullite, carborundum, stainless steel, silicon carbide, steatite, earthenware, porcelain, iron, and various kinds of ceramic materials.

The inactive refractory substance, for example, is in a granular state. The layer of such an inactive refractory substance is not always uniformly packed throughout the entire volume thereof. For the purpose of effectively cooling the reaction gas, however, the layer of the inactive refractory substance is preferably packed substantially uniformly throughout the entire volume thereof. This rule similarly applies to the other inactive refractory substance than the granular shape.

One of the operational function of the inactive refractory substance layer consists in rapid cooling of the product-containing gas flowed from the upstream side catalyst layer to adjust the temperature thereof to a range proper for the oxidation reaction in the downstream side catalyst layer when the temperature of chamber A is lower than that of chamber B. The inactive refractory substance layer, therefore, must be so disposed as to have a length enough for the operational function to be fully manifested.

In this invention, therefore, the inactive refractory substance layer is given a length enough for cooling the reaction gas flowed from the upstream side catalyst layer to a temperature suitable for the downstream side catalyst layer, and the catalyst in the outlet part of the upstream side catalyst layer and the catalyst in the inlet part of the downstream side catalyst layer are so disposed as not to be exposed to the thermal effect of the intermediate tube sheet. Further, the length of an inactive refractory substance layer may be decreased because the transfer of heat medium between the chambers is relaxed and the mutual thermal effect on the chambers is lowered. The reaction tube packed with the catalyst, i.e., the reactor can be decreased in length.

To be specific, the inactive refractory substance layer is so long that the reaction gas entering the downstream side catalyst layer from the inactive refractory substance layer, namely the reaction gas in the inlet part of the downstream side catalyst layer, is cooled to below the temperature of the catalyst inlet plus 15° C. in the case that the heat medium is co-currently flowed to the raw material or the reaction gas.

The other operational function of the inactive refractory layer consists in not only preventing from inducing pressure drop based on the impurities contained in the reaction gas flowed from the upstream side reaction layer, such as the molybdenum component sublimited from the upstream side catalyst layer and high boiling substances like by-produced terephthalic acid which occur in the production of acrylic acid while passing the inactive refractory substance layer but also preventing such impurities from directly entering the downstream side catalyst layer and deteriorating the catalytic properties thereof. For the sake of this operational function, it suffices to decrease the percentage of voids in the inactive refractory substance layer. If this percentage of voids is decreased excessively, however, the excess will be at a disadvantage in increasing the pressure drop. In this invention, therefore, the percentage of voids in the inactive refractory substance layer is generally in the range of 40–99.5%, preferably 45–99%. The term "percentage of voids" as used in this invention is defined by the following formula:

$$\text{Percentage of voids } (\%) = \{(X-Y)/X\} \times 100$$

wherein

X denotes the volume of the inactive refractory substance layer, and

Y the real volume of the inactive refractory substance (the term "real volume" in the case of a ring, for example, means the volume of the real entity of the ring excluding the empty part at the center thereof).

If the percentage of voids is less than 40%, the shortage will be at a disadvantage in unduly increasing the pressure drop. Conversely, if this percentage exceeds 99.5%, the excess will be at a disadvantage in degrading the function of cooling the reaction gas as well as lowering the function of capturing the impurities.

The inactive refractory substance is preferably inserted into the inlet part of the upstream side catalyst for the purpose of preheating the raw material gas, since this insertion brings the advantage of increasing the yield of the product.

With reference to FIG. 1, the raw material gas is supplied to the reactor 1 through the lower part thereof, brought into contact with the catalyst to give a desired product, and discharged from the reactor through the upper part thereof. The reaction gas may be supplied to the reactor through the upper part thereof, provided packing sequence of the catalysts into the reactor is changed.

In chamber A, a heat medium discharged through heat medium outlets 12 of an annular conduit 9a which is disposed on the outer periphery of the reactor 1 and which is equipped with a plurality of openings communicating with the reactor 1, is cooled by a heat exchanger 15a. The cooled heat medium, by means of a known pump 16a such as a volute pump or an axial-flow pump, is transferred through heat medium inlets 11a and introduced into chamber A through an annular conduit 10a which is disposed round the outer periphery of the reactor 1 and which is provided with a plurality of openings communicating with the reactor 1. The heat medium enters the interior of the reactor 1 through the nearly whole of the periphery of the reactor and, while contacting the bundle of reaction tubes 4, absorbs the heat generated therein when the reaction is of an exothermic type, transfers to the center of the reactor, and ascends the holes of a donut type baffle plate 19a. Further, the heat medium flows substantially horizontally along the plates and, while contacting the bundle of reaction tubes 4 in the same manner as above, absorbs the reaction heat, transfers toward nearly the inner peripheral part of the reactor, and ascends between the outer peripheral part of the disc type baffle plate 18a and the wall of reactor. Thereafter, it transfers while repeating the actions mentioned above to the annular conduit 9a disposed around the outer periphery of the reactor 1.

In chamber B, the heat medium is circulated in the same manner as in chamber A.

The circulation of heat mediums, when necessary, may be reversed in either or both of chambers A and B. However the heat medium is preferably passed through these pumps 16ab after it has been cooled to a relatively low temperature by passage through the heat exchangers 15ab from the viewpoint of protecting the pumps 16ab.

The conditions for gas phase catalytic oxidation of a raw material gas containing propylene with molecular oxygen may be those of any known methods available for the reaction. When acrolein is produced by oxidizing propylene in the presence of an upstream side catalyst, for example, the propylene concentration in the raw material gas is in the range of 3–15% by volume, the ratio of the molecular oxygen to propylene is in the range of 1–3, and the remainder of the raw material gas comprises nitrogen, steam, carbon oxides, and propane.

Though air is advantageously used as the source for the molecular oxygen, an oxygen-enriched air or pure oxygen may be used as occasion demands. Oxidation reactions are performed by an one-pass or recycling method. Preferably, the reaction temperature may be in the range of 250° C.–450° C., the reaction pressure in the range of atmospheric pressure to five atmospheres, and the space velocity in the range of 500–3000 $h^{-1}$ (STP).

Then, for the purpose of producing acrylic acid, the acrolein-containing gas produced by the upstream side reaction mentioned above may be sequentially supplied at a reaction temperature (the temperature of the heat medium in the reactor) in the range of 200–400° C., preferably 220–350° C., at a space velocity in the range of 300–5,000 $h^{-1}$ (STP) to the individual reaction tubes, in the upper chamber partitioned with the intermediate tube sheet within the shell, packed with the downstream side catalyst so as to produce acrylic acid by means of the downstream side reaction.

The reactor of this invention can be fully adopted even in such a reaction that the difference between the reaction temperatures of the reactions is in the range of 20–80° C., e.g., a reaction that comprises oxidizing propylene into acrolein and further oxidizing acrolein into acrylic acid.

The reactor of this invention is suitable, as described above, for performing continuously the reaction of oxidation. Other reactions to which the reactor of this invention is applied and other embodiments of this application will be described below.

In the production of methacrolein by the reaction of gas phase catalytic oxidation of an isobutylene-containing raw material gas in the presence of an upstream side catalyst, the isobutylene concentration in the raw material gas may be in the range of 1–10% by volume, the concentration of molecular oxygen to isobutylene is in the range of 3–20% by volume, a steam content is in the range of 0–60% by volume, and the remainder of the raw material gas comprises nitrogen, steam, and carbon oxides. Though air is advantageously used as the source for the molecular oxygen, an oxygen-enriched air or pure oxygen may be used as occasion demands. Preferably, the reaction temperature is in the range of 250° C.–450° C., the reaction pressure in the range of atmospheric pressure to five atmospheres, and the space velocity in the range of 300–5000 $h^{-1}$ (STP).

Further, the methacrolein-containing gas produced by the upstream side reaction is sequentially supplied to the region (the upper chamber partitioned with the intermediate tube sheet) in which the reaction tubes inside the shell are packed with an oxidation catalyst (downstream side catalyst) containing molybdenum and phosphorus for the formation of methacrylic acid, at a reaction temperature (the temperature of the heat medium in the reactor) in the range of 100–380° C., preferably 150–350° C., at a space velocity in the range of 300–5,000 $h^{-1}$ (STP) so as to produce methacrylic acid by the downstream side reaction.

Incidentally, the conventional catalysts that produce methacrolein from isobutylene and methacrylic acid from the methacrolein can be used.

To be specific, the upstream side catalyst is preferred to be a composition represented by the formula:

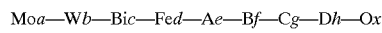
Mo$a$—W$b$—Bi$c$—Fe$d$—A$e$—B$f$—C$g$—D$h$—O$x$ wherein
Mo, W, and Bi respectively denote molybdenum, tungsten, and bismuth,
Fe denotes iron,
A nickel and/or cobalt,
B at least one element selected from the group consisting of alkali metals, alkaline earth metals, and thallium,
C at least one element selected from the group consisting of phosphorus, tellurium, antimony, tin, cerium, lead, niobium, manganese, and zinc,
D at least one element selected from the group consisting of silicon, aluminum, titanium, and zirconium,
O oxygen, and
a, b, c, d, e, f, g, h, and x respectively denote the numbers of atoms of Mo, W, Bi, Fe, A, B, C, D, and O, which fall respectively in the ranges of b 0–10, c=0.1–10, d=0.1–20, e=2–20, f=0.001–10, g=0–4, h=0–30, and x assumes the numerical value decided by the states of oxidation of the relevant elements where a=12 is fixed.

The downstream side catalyst is not particularly restricted so long as it comprises one or more oxidation catalysts containing molybdenum and phosphorus as main components. It is preferred to be a phosphomolybdic acid type heteropoly acid or a metal salt thereof. Specifically, it is preferred to be a composition represented by the formula:

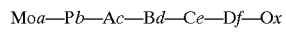
Mo$a$—P$b$—A$c$—B$d$—C$e$—D$f$—O$x$ wherein
Mo denotes molybdenum,
P denotes phosphorus, A denotes at least one element selected from the group consisting of arsenic, antimony, germanium, bismuth, zirconium, and selenium,
B at least one element selected from the group consisting of copper, iron, chromium, nickel, manganese, cobalt, tin, silver, zinc, palladium, rhodium, and tellurium,
C at least one element selected from the group consisting of vanadium, tungsten, and niobium,
D at least one element selected from the group consisting of alkali metals, alkaline earth metals, and thallium,
O oxygen, and
a, b, c, d, e, f, and x respectively denote the atomic ratios respectively of Mo, P, A, B, C, D, and O, which falls in the ranges of b=0.5–4, c=0–5, d=0–3, e=0–4, f=0.01–4, and x denotes the numerical value decided by the state of oxidation of the relevant elements where a=12 is fixed.

Further, when such chambers A and B as illustrated in FIG. 1, for example, are utilized and a known catalyst is used in the production of phthalic anhydride from ortho-xylene and/or naphthalene, generally it is necessary to adopt a temperature in the range of 300–400° C. on the upstream side and a temperature in the range of 350–450° C. on the downstream side and maintain a catalyst of one and the same composition at a temperature difference in the range of 30–60° C. in the two chambers A, B. These conditions are readily fulfilled.

When a known catalyst is used in the production of maleic anhydride from benzene, favorable results are generally brought about by adopting a temperature in the range of 320–400° C. on the upstream side and a temperature in the range of 350–450° C. on the downstream side and maintain a catalyst of one and the same composition at a temperature difference in the range of 20–50° C. in the two chambers. Again these conditions are readily fulfilled.

EXAMPLES

Now, this invention will be described more specifically below with reference to examples. These examples are intended to aid in comprehension of this invention and not meant to impose any restriction on the contents of the invention.

Hydraulic Test

In the case of two chambers, water is fully introduced into an upper chamber but the other lower chamber is empty. A pressure, for instance 39226.6 Pa (0.4 Kg/cm$^2$) is applied to the upper chamber by raising a transparent pipe from an upper part of the upper chamber (as required: when the height from the intermediate tube sheet is less than 4 m) and then filing water into the pipe at a height of 4 m from the intermediate tube sheet. In the case of the water surface in the chamber filled with water and the lower chamber being opened to atmosphere, respectively, the decrease of the water level (the amount of leakage) is measured at the pressure difference being 39226.6 Pa (0.4 Kg/cm$^2$). Conversely, when a further measurement is performed for the lower chamber, the reactor is overturned and the same procedure is repeated.

Example 1

Synthesis of acrylic acid by the oxidation of propylene was performed by the use of a vertical shell-and-tube type reactor equipped with expansion joints, 24 reaction tubes of steel each measuring 6 m in length, 25.0 mm in inside diameter, and 29.0 mm in outside diameter and having an intermediate tube sheet at an intermediate height as illustrated in FIG. 1.

The amount of water migrating from the upper chamber to the lower chamber through the intermediate tube sheet partitioning these two chambers was 0.1 ml/hour per reaction tube under the condition of a pressure difference of 39226.6 Pa (0.4 kg/cm$^2$). Then, the amount of water migrating from the lower chamber to the upper chamber through the intermediate tube sheet partitioning these two chambers was 0.1 ml/hour per reaction tube under the condition of a pressure difference of 39226.6 Pa (0.4 kg/cm$^2$). In the hydraulic test, the relation, amount of leakage (ml/hour per reaction tube)$\leq 1.27 \times 10^{-5} \times$pressure difference (Pa) {1.25$\times$pressure difference (kg/cm$^2$)}, (namely $1.27 \times 10^{-5 \times 39226.6}=0.5$), was invariably satisfied.

The catalyst used in this reaction was prepared as a catalyst for the production mainly of acrolein from propylene. In 150 liters of purified water which was kept heated and stirred, 100 kg of ammonium molybdate and 6.3 kg of ammonium paratungstate were dissolved. To the resultant solution, an aqueous nitrate solution separately prepared by dissolving 75.6 kg of cobalt nitrate in 100 liters of purified water, 19 kg of ferric nitrate in 30 liters of purified water, and 27.5 kg of bismuth nitrate in 30 liters of purified water incorporating therein 6 liters of concentrated nitric acid respectively and then mixing the produced aqueous solutions was added dropwise. Subsequently, a solution having 14.2 kg of an aqueous 20 wt % silica sol solution and 0.29 kg of potassium nitrate dissolved in 15 liters of purified water was added thereto. The suspension thus obtained was heated and stirred till evaporation to dryness and then dry pulverized. The powder consequently obtained was molded in cylinders 5 mm in diameter and calcined in a stream of air at 460° C. for six hours to produce a catalyst (having a composition of Mo 12, Bi 1.2, Fe 1, Co 5.5, W 0.5, Si 1, and K 0.06 in molar ratio).

As the catalyst for use on the downstream side, a catalyst represented by the following composition (excluding oxygen) was prepared in accordance with the method popular in the art: $Mo_{12}V_{5.5}W_{1.2}Cu_{2.2}Sb_{0.5}$.

This catalyst was produced by the following method. In 500 liters of purified water which was kept heated and stirred, 100 kg of ammonium molybdate, 15.3 kg of ammonium paratungstate, and 30.4 kg of ammonium metavanadate were placed and dissolved. To the resultant solution, a solution obtained by adding 25 kg of copper nitrate and 3.4 kg of antimony trioxide to 50 liters of purified water was added. The produced mixed solution and 350 kg of a silica-alumina carrier having an average particle diameter of 5 mm added thereto were together evaporated to dryness to effect deposition of a catalytic component on the carrier and then calcined at 400° C. for six hours to produce a catalyst.

First, the reaction tubes were each packed with 130 mm (note that it means the height of reaction tube when filled) of spheres of alundum 8 mm in diameter, 2790 mm of the upstream side catalyst was deposited, 240 mm of spheres of alundum 8 mm in diameter (percentage of voids: 45%) was deposited for cooling the reaction gas, and 2200 mm of the downstream side catalyst was deposited thereon.

The raw material gas composed of 7.0 vol. % of propylene, 12.6 vol. % of oxygen, 10.0 vol. % of steam, and 70.4 vol. % of an inert gas comprising nitrogen, etc. was introduced and held in contact with the upstream side catalyst for a retention time of 2.8 seconds (as reduced to NTP) to produce a reaction at 310° C. on the upstream side and 265° C. on the downstream side.

The results of the reaction are shown in Table 1 below.

Comparative Example 1

A reaction was performed by following the procedure of Example 1 while using a reactor which had reaction tubes not expanded to be tightly fitted to an intermediate tube sheet. (Amount of leakage per test tube=1 liter/h>0.5=1.27$\times 10^{-5} \times$39226.6).

The test results are shown in Table 1.

TABLE 1

|  |  | Example 1 | Comparative Example 1 |
|---|---|---|---|
| Tube expansion in the part of shield |  | Yes | No |
| Groove |  | Two grooves | No |
| Results of reaction | Propylene conversion | 97.5 mol % | 96.2 mol % |
|  | Yield of acrylic acid | 88.6 mol % | 86.4 mol % |

Example 2

Synthesis of methacrylic acid by the oxidation of isobutylene was performed by the use of a vertical shell-and-tube type reactor equipped with 24 reaction tubes of steel each measuring 6 m in length, 25.0 mm in inside diameter, and 29.0 mm in outside diameter and having an intermediate tube sheet at an intermediate height as illustrated in FIG. 1.

The amount of water migrating from the upper chamber to the lower chamber through the intermediate tube sheet partitioning these two chambers was 0.1 ml/hour per reaction tube under the condition of a pressure difference of 39226.6 Pa (0.4 kg/cm$^2$). Then, the amount of water migrating from the lower chamber to the upper chamber through the intermediate tube sheet partitioning these two chambers was 0.1 ml/hour per reaction tube under the condition of a pressure difference of 39226.6 Pa (0.4 kg/cm$^2$). In the hydraulic test, the relation, amount of leakage (ml/hour per reaction tube)$\leq 1.27 \times 10^{-5} \times$pressure difference (Pa) {1.25$\times$pressure difference (kg/cm$^2$)}, (namely $1.27 \times 10^{-5 \times 39226.6}=0.5$), was invariably satisfied.

The catalyst used in this reaction was prepared as a catalyst for the production mainly of methacrolein from isobutylene. In 150 liters of purified water which was kept heated and stirred, 100 kg of ammonium molybdate and 6.3 kg of ammonium paratungstate were dissolved. To the resultant solution, an aqueous nitrate solution separately prepared by dissolving 75.6 kg of cobalt nitrate in 20 liters of purified water, 28.6 kg of ferric nitrate in 30 liters of purified water, and 34.3 kg of bismuth nitrate in 30 liters of purified water incorporating therein 8 liters of concentrated nitric acid respectively and then mixing the produced aqueous solutions was added dropwise. Subsequently, a solution having 14.2 kg of an aqueous 20 wt % silica sol solution and 4.6 kg of cesium nitrate dissolved in 20 liters of purified water was added thereto. The suspension thus obtained was heated and stirred till evaporation to dryness and then dry pulverized. The powder consequently obtained was molded in cylinders 5 mm in diameter and calcined in a stream of air at 500° C. for six hours to produce a catalyst (having a composition of Mo 12, Bi 1.5, Fe 1.5, Co 5.5, W 0.5, Si 1, and Cs 0.5 in molar ratio).

As the catalyst for use on the downstream side, a catalyst represented by the following composition (excluding oxygen) was prepared in accordance with the method popular in the art: $Mo_{12}P_{1.2}V_{1.2}Cs_{1.4}Cu_{0.1}$.

This catalyst was produced by the following method. In 400 liters of deionized water which was kept heated, 100 kg of ammonium paramolybdate and 6.6 kg of ammonium metavanadate were placed and dissolved. The resultant solution, 6.5 kg of orthophosphoric acid (85% by weight) added thereto, and an aqueous solution obtained by dissolving 12.9 kg of cerium nitrate and 1.1 kg of copper nitrate dissolved in 100 liters of deionized water and added thereto were thoroughly stirred together and meantime superheated and concentrated. The resultant slurry was dried at 230° C. for 15 hours and then pulverized. The produced powder and water added thereto as a foaming auxiliary were molded in cylinders 5.5 mm in outside diameter and 6.5 mm in length, dried, and thereafter calcined in a stream of nitrogen at 400° C. for three hours and subsequently in a stream of air at 400° C. for two hours to produce a catalyst.

First, the reaction tubes were each packed with 890 mm (note that it means the height of reaction tube when filled) of spheres of alundum 8 mm in diameter, 2000 mm of the upstream side catalyst was deposited, 240 mm of spheres of alundum 8 mm in diameter (percentage of voids: 45%) was deposited for cooling the reaction gas, and 2800 mm of the downstream side catalyst was deposited thereon.

The raw material gas composed of 4.0 vol. % of isobutylene, 13.1 vol. % of oxygen, 6.0 vol. % of steam, and 76.9 vol. % of an inert gas comprising nitrogen, etc. was introduced and held in contact with the upstream side catalyst for a retention time of 3.0 seconds (as reduced to NTP) to produce a reaction at 350° C. on the upstream side and 290° C. on the downstream side.

The results of the reaction are shown in Table 2 below.

Comparative Example 2

A reaction was performed by following the procedure of Example 1 while using a reactor having intervals between reaction tubes and an intermediate tube sheet adjusted at about 0.8 mm (amount of leakage: same as in Comparative Example 1).

The results obtained were shown in Table 2.

TABLE 2

|  |  | Example 2 | Comparative Example 2 |
|---|---|---|---|
| Tube expansion in the part of shield |  | Yes | No |
| Groove |  | Two grooves | No |
| Results of reaction | Isobutylene conversion | 100.0 mol % | 100.0 mol % |
|  | Methacrylic acid yield | 67.0 mol % | 65.3 mol % |

Example 3 and Comparative Example 3

The same reactor as used in Example 1 (Example 3) and a reactor equaling the reactor of Example 1 while omitting an expansion joint (Comparative Example 3) were operated for three years and thereafter subjected to hydraulic test to determine the amount of migration between adjacent chambers.

The amount of leakage per reaction tube from the upper chamber to the lower chamber under the condition of pressure difference of 39226.6 Pa (0.4 kg/cm$^2$) was as shown below.

Reactor Using Expansion Joints (Example 3): 0.12 Ml/Hour

Reactor Using No Expansion Joint (Comparative Example 3): 0.52 ml/hour

A clear difference in the amount of leakage was observed between the presence and the absence of an expansion joint. The results indicate that the provision of expansion joints could decrease the leakage through the intermediate tube sheet and permitted accurate control of the reaction temperature.

The entire disclosure of Japanese Patent Application No. 11-315469 filed on Nov. 5, 1999 including specification, claims, drawings and summary are incorporated herein by reference in its entirety.

What is claimed is:

1. A shell-and-tube type reactor comprising:
   a shell in which a plurality of reaction tubes are held with a first tube sheet and a second tube sheet in the reactor;
   a raw material inlet equipped in the first tube sheet side of the shell;
   a product outlet equipped in the second tube sheet side of the shell;
   an intermediate tube sheet provided horizontally in the shell wherein the reaction tube is expanded to at least one groove formed in the reaction tube-fixing part of the intermediate tube sheet for substantially shielding spaces between the tubes and partitioned with the intermediate tube sheet to form a shield for partitioning a plurality of chambers; and
   an expansion joint formed around the periphery of each of the chambers, wherein the expansion joints are capable of absorbing distortion generated by an increase or decrease of heat of a heat medium,
   and wherein a migration of the heat medium between the chambers partitioned with the shield is repressed when the chambers are substantially closed, and a reaction or treatment in the one chamber is performed at a different temperature from that in the other chamber,
   and wherein an amount of water migrating from the upper chamber to the lower chamber, and from the lower chamber to the upper chamber, fulfills the relation, amount of leakage (ml/hour per reaction tube) $\leq 1.27 \times 10^{-5} \times$ pressure difference (Pa), in a hydraulic test.

2. A reactor according to claim 1, wherein a number of the grooves which is provided to the tube sheet and which faces to the reaction tube is two.

3. A reactor according to claim 1, wherein a number of the grooves which is provided to the tube sheet and which faces to the reaction tube is three.

4. A reactor according to claim 1, wherein a number of the chambers is two to form an upper chamber and a lower chamber, and a reaction or treatment in the upper chamber is performed at a different treatment from that in the lower chamber.

5. A reactor according to claim 1, wherein the expansion joint is roughly semicircular, with the inner face of the joint directed toward the inner side of the reactor and the upper and lower ends of the joint connected to the almost horizontally cut shell of the reactor.

6. A reactor according to claim 1 further comprising a baffle plate substantially horizontally disposed in the reactor.

7. A reactor according to claim 1 further comprising a circular conduit for transferring a heat medium around the reactor.

8. A reactor according to claim 4, wherein different kinds of reactions are performed.

9. A method for producing (meth)acrylic acid by the reaction of catalytic gas phase oxidation which comprises the step of contacting a propylene-containing gas or an isobutylene-containing gas to a catalyst filled in a reactor set forth in claim 1.

* * * * *